US011135385B2

(12) United States Patent
Ali et al.

(10) Patent No.: US 11,135,385 B2
(45) Date of Patent: Oct. 5, 2021

(54) NEONATAL LARYNGEAL MASK AIRWAY

(71) Applicant: Samreen Mehar Ali, Saint Louis, MO (US)

(72) Inventors: Ayoob Ali, Saint Louis, MO (US); Samreen Mehar Ali, Saint Louis, MO (US)

(73) Assignee: Samreen Mehar Ali, St. Louis, MO (US)

( * ) Notice: Subject to any disclaimer, the term of this patent is extended or adjusted under 35 U.S.C. 154(b) by 0 days.

(21) Appl. No.: 13/738,882

(22) Filed: Jan. 10, 2013

(65) Prior Publication Data
US 2014/0014113 A1    Jan. 16, 2014

Related U.S. Application Data

(60) Provisional application No. 61/585,213, filed on Jan. 10, 2012.

(51) Int. Cl.
*A61M 16/04* (2006.01)

(52) U.S. Cl.
CPC .... *A61M 16/0434* (2013.01); *A61M 16/0409* (2014.02); *A61M 16/0431* (2014.02); *A61M 16/0463* (2013.01); *A61M 2202/0488* (2013.01)

(58) Field of Classification Search
CPC .. A61M 16/00; A61M 16/04; A61M 16/0402; A61M 16/0404;
(Continued)

(56) References Cited

U.S. PATENT DOCUMENTS

| 4,256,099 A | 3/1981 | Dryden |
| 4,509,514 A | 4/1985 | Brain |

(Continued)

FOREIGN PATENT DOCUMENTS

| CN | 202376585 | 8/2012 |
| EP | 0712638 A1 | 5/1996 |

(Continued)

OTHER PUBLICATIONS

Tetsuro Kagawa, M.D. and Hidefumi Obara, M.D. "An Easy Formula to Remember the Laryngeal Mask Airway Size-Patient Weight Relationship" Feb. 2000, Lippincott Williams & Wilkins, Inc., Anesthesiology, vol. 92, No. 2, p. 631.*

(Continued)

*Primary Examiner* — Samchuan C Yao
*Assistant Examiner* — Ned T Heffner
(74) *Attorney, Agent, or Firm* — Michael S. Young; Michael S. Young IP Law LLC (57) ABSTRACT

A neonatal laryngeal mask airway (NLMA) can be used for airway management in the neonate in emergent situations, e.g., respiratory distress syndrome after premature birth, and nonemergent situations, e.g., elective surgery. The NLMA includes a back plate and a cuff. The back plate provides a shelf, a back plate opening, and a wall, which is perpendicular to the shelf, that surrounds a portion of the back plate opening. The cuff is coupled completely around a perimeter of the back plate. The cuff is configured for inflation from an uninflated state to an inflated state in a patient with a pharynx, a larynx with a laryngeal inlet, and a trachea. In the inflated state, the cuff forms a seal around the laryngeal inlet to isolate the larynx from the pharynx, and the back plate is configured to guide a catheter inserted through the back plate opening into the trachea.

20 Claims, 8 Drawing Sheets

(58) Field of Classification Search
CPC .... A61M 16/0434–0456; A61M 16/06; A61M 25/00; A61M 25/0029; A61M 25/10–1025; A61M 25/002; A61M 25/003; A61M 25/006; A61M 25/0024; A61M 25/1043–1097
USPC .......................... 128/200.24, 200.26, 206.26, 128/207.14–207.17, 205.23, 204.23; 604/93.01
See application file for complete search history.

(56) References Cited

U.S. PATENT DOCUMENTS

| | | | |
|---|---|---|---|
| 4,688,568 | A | 8/1987 | Frass |
| 4,995,388 | A | 2/1991 | Brain |
| 5,443,063 | A | 8/1995 | Greenberg |
| 5,871,012 | A | 2/1999 | Neame |
| 6,261,401 | B1* | 7/2001 | Pagan ................. 156/182 |
| 6,634,354 | B2 | 10/2003 | Christopher |
| 6,668,821 | B2 | 12/2003 | Christopher |
| 6,705,318 | B1 | 3/2004 | Brain |
| 6,895,966 | B2 | 5/2005 | Christopher |
| 7,096,868 | B2 | 8/2006 | Tateo |
| 7,159,589 | B2* | 1/2007 | Brain ............... A61M 16/04 128/207.14 |
| 7,493,901 | B2 | 2/2009 | Brain |
| 7,712,467 | B2 | 5/2010 | Mongeon |
| 7,938,118 | B2 | 5/2011 | Kessler |
| 8,215,307 | B2 | 7/2012 | Nasir |
| 8,267,090 | B2 | 9/2012 | Cegla |
| 2001/0015207 | A1* | 8/2001 | Pagan ............... A61M 16/04 128/207.15 |
| 2003/0037790 | A1 | 2/2003 | Brain |
| 2003/0101998 | A1* | 6/2003 | Zocca et al. ............. 128/207.15 |
| 2005/0279361 | A1* | 12/2005 | Chang ............... A61M 16/04 128/207.14 |
| 2008/0078402 | A1 | 4/2008 | Mongeon |
| 2008/0200776 | A1 | 8/2008 | Schermeier et al. |
| 2008/0276936 | A1* | 11/2008 | Cook ..................... 128/204.18 |
| 2011/0017388 | A1 | 1/2011 | Brain |

FOREIGN PATENT DOCUMENTS

| | | |
|---|---|---|
| WO | 95/32754 | 7/1995 |
| WO | 02/092144 | 11/2002 |
| WO | WO-02/092144 A2 | 11/2002 |
| WO | WO 95132754 A2 | 3/2003 |
| WO | 2011131974 A1 | 10/2011 |
| WO | 2012032290 A8 | 3/2012 |

OTHER PUBLICATIONS

Barbosa, et al.; "ProSeal™ laryngeal mask airway for surfactant administration in the treatment of respiratory distress syndrome in a premature infant"; Rev Bras Ter Intensiva.; 24(2); 2012; 4 pages.
PCT/US2013/054592; International Search Report and Written Opinion; dated Dec. 6, 2013; 5 pages.
The Use of LMA in Newborn Resuscitation, R Vadhera, The Internet Journal of Anesthesiology, 1996, vol. 1, No. 4.
Alternative Formula for Laryngeal Mask Airway™ Size Selection, Shuichi Hirai, M.D., Reiko Nakamura, M.D., Nobuhiro Maekawa, M.D., Anesthesiology Feb. 2004; vol. 100: No. 2, p. 460.

* cited by examiner

NEONATAL LARYNGEAL MASK AIRWAY

CROSS-REFERENCE TO RELATED APPLICATIONS

This nonprovisional application claims priority to U.S. Prov. Pat. App. No. 61,585,213 filed on Jan. 10, 2012, entitled "Neonatal Laryngeal Mask Airway (NLMA).

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

FIELD OF THE DISCLOSURE

This disclosure concerns a medical instrument used in neonatal resuscitation.

BACKGROUND OF THE DISCLOSURE

British anesthesiologist Dr. Archie Brain invented the laryngeal mask airway (LMA) in 1981. An artificial airway should be able to overcome airway obstruction rapidly and easily without trauma even if the artificial airway is used by an unskilled clinician. Tracheal intubation (also known herein as endotracheal intubation or intratracheal intubation or may be simply referred to as intubation) was introduced in the late $19^{th}$ century, but the LMA has brought a truly revolutionary change in the airway management in the pediatric and adult patient populations.

The LMA is used in anesthesia and in emergency medicine, including the intensive care unit setting, for airway management. The LMA includes a tube with an inflatable cuff, and the LMA is inserted into the pharynx of a patient. The LMA may cause less pain and coughing in the patient than an endotracheal tube, and the LMA is much easier for the clinician to insert into a correct location. The LMA is a supraglottic device that can be used to administer positive pressure ventilation (PPV) in adults, pediatric and neonatal patients.

Approximately 3.5 million babies are born annually in the United States. 6% of newborns require advanced life support in the delivery rooms. Most of the neonatal intensive care units are covered by neonatologists, who are available 24 hours a day to attend high risk deliveries. The newborns who weigh less than 1500 grams (g) usually require some sort of resuscitation at birth. Positive pressure ventilation is recommended in different modalities if required for a newborn with respiratory distress. The American Heart Association guidelines for neonatal resuscitation recommend that positive pressure ventilation (PPV), when indicated, be administered by bag and mask.

The LMA has been used successfully and effectively in achieving a reliable airway in adult and pediatric populations, especially in cases of difficult airway management. Due to the nature of the neonatal anatomy, there is no laryngeal mask airway available to address difficult airway issues in the neonatal population, including premature infants.

Insertion of an endotracheal tube is not always easy for the clinician, and intratracheal intubation requires training and practice for the clinician to establish successful and effective airway management. Resuscitation by face mask and bag or endotracheal tube intubation both require skill by the clinician to resuscitate newborn infants, especially premature infants. These concerns are among the driving force behind development of the neonatal laryngeal mask airway (NLMA) that is disclosed herein.

There are many studies now published regarding the successful use of LMA in children. The experience with the LMA in infants though is very limited. Initially, the LMA was designed for use in adults; however, cadaveric studies in infants demonstrated that despite the anatomic difference between adult and pediatric airways the LMA works in pediatric patients. The size 1 LMA is a smaller LMA available at present for infants weighing more than 2.5 kg for management of a difficult airway.

Airway management is the paramount feature of resuscitation in neonates, especially infants birth weight less than 1500 g. Airway management during neonatal resuscitation is currently achieved either with a face mask (FM) or endotracheal intubation with a tracheal tube (TT). Bag and face mask ventilation can occasionally be difficult, and tracheal intubation may be impossible due to lack of skill by the clinician or the presence of severe congenital abnormalities in the oropharynx of the neonate. Now, we have the neonatal laryngeal mask airway (NLMA) as a potential third option that bridges the gap between the FM and TT in difficult airways of neonates by taking into account specific anatomy and clinical needs of the neonate.

The NLMA Size 1 (NLMA-1) is designed to use in full term infants and Size 0 (NLMA-0) and Size 00 (NLMA-00) are designed for pre-term neonates who require surfactant administration to the trachea for respiratory distress secondary (RDS) secondary to hyaline membrane disease, pneumonia and stiff lungs. The NLMA could, also, be used for maintenance of the difficult airway in infants.

BRIEF SUMMARY OF THE DISCLOSURE

The present disclosure describes the NLMA that can be used to administer surfactant to full term and premature neonates with respiratory distress syndrome (RDS) without endotracheal intubation. Endotracheal intubation is not only difficult in neonates, but endotracheal intubation is also traumatic. The NLMA will allow the clinician to give surfactant without requiring endotracheal intubation of the neonate. Further, the LMA will be very effective in neonatal resuscitation, including premature infants.

The NLMA includes a back plate and a cuff. The back plate provides a shelf, a back plate opening, and a wall, which is perpendicular to the shelf, that surrounds a portion of the back plate opening. The cuff is coupled completely around a perimeter of the back plate. The cuff is configured for inflation from an uninflated state to an inflated state in a patient with a pharynx, a larynx with a laryngeal inlet, and a trachea. In the inflated state, the cuff forms a seal around the laryngeal inlet to isolate the larynx from the pharynx, and the back plate is configured to guide a catheter inserted through the back plate opening into the trachea.

DETAILED DESCRIPTION OF THE DISCLOSURE

The Neonatal Laryngeal Mask Airway (NLMA) is the future revolution of resuscitation in the neonatal population. The NLMA will be very effective in neonatal resuscitation including premature infants. These artificial airway devices can be used to facilitate ventilation of the infant's lungs by establishing airway in emergent situations when standard methods to establish an airway have failed. Of course, the NLMA can be used in non-emergent situations. For example, the NLMA can, also, be used to establish a patent airway for anesthesia during a surgical procedure. Additionally, the NLMA enables the clinician to administer surfactant in premature infants and near full term infants suffering with respiratory distress syndrome (RDS) without endotracheal intubation.

The NLMA is not only an effective and safe way of resuscitation of the premature infant compared to ventilation with a bag and mask resuscitation of the premature infant, but the NLMA can be a useful and minimally invasive or noninvasive method for the administration of surfactant therapy especially in term and pre-term infants. Currently, there is no such device available to administer surfactant without requiring intubation, and there is no LMA available for premature neonates. The NLMA is designed to administer surfactant to the term and pre-term infants with respiratory distress syndrome (RDS) without requiring endotracheal intubation of the infant. The NLMA can, also, be used for the administration of positive pressure ventilation (PPV) in patients, including in term and pre-term neonatal patients.

Endotracheal intubation is not only difficult in neonates. but it is also traumatic. The clinician requires extensive training and practice in order to successfully intubate premature infants. This NLMA will give an advantage to pediatricians and neonatologists and less skilled healthcare providers to establish an emergent airway in these premature infants, as well as provide for the ability to give surfactant without being endotracheal intubation.

NLMA-00 is specifically designed for premature infants smaller than an infant with a gestational age of 30 weeks or birth weight of 1500 g. NLMA-0 is specifically designed for premature infants of gestational age from 30 weeks to 35 weeks or birth weight of 1500 g to 2500 g. NLMA-1 is specifically designed for infants of gestational age from 35 weeks to 3 months of life or birth weight 2500 g to 5000 g.

A catheter can be inserted into the trachea for surfactant administration in the neonate using the NLMA. The size 1, 0 and 00 NLMA can be inserted into the neonate in one of the two ways either in the standard fashion, with the aperture facing anteriorly, or in reverse orientation with the aperture facing the roof of the mouth followed by turning the NLMA through 180° on reaching the posterior pharyngeal wall. Once the NLMA is inserted, the cuff is inflated with 2-4 ml air to create the seal of the NLMA around the glottis. Unlike traditional LMA, the NLMA does not have ribs to prevent incursion of the epiglottis into the NLMA, because neonates do not have a well-developed epiglottis that would block function of the NLMA. Then, a 6 Fr. catheter can be introduced through the connector of the NLMA and advanced through the NLMA to a precalculated distance to advance the catheter through the opening at the base of the NLMA. A tip of the catheter is passed through the glottis opening into the trachea. This position of the catheter is a desirable position for surfactant administration.

The NLMA is designed to administer surfactant to the trachea without use of laryngoscope for endotracheal intubation. The NLMA is less traumatic to local tissues and the respiratory tract of the infant then intubation. The NLMA makes it very easy for the clinician to administer surfactant, and there is no risk of endobronchial or esophageal intubation by physicians in training. The NLMA can be used to obtain a clear airway more rapidly than with endotracheal intubation and fewer failures.

The NLMA includes of an inflatable cuff (also known herein as the laryngeal cuff or is simply known as the cuff) and a back plate (also known herein as the roof plate or the laryngeal plate or laryngeal roof plate) with a curved shape. The curved shape of the back plate creates a channel that helps guide the catheter along its path towards the trachea, for example. The outer surface of the back plate connects with a proximal part of the laryngeal cuff. The back plate is connected to the laryngeal cuff margins internally forming separation between a laryngeal portion of the back plate on the inner surface and a pharyngeal portion of the back plate on the outer surface of the neonate when the cuff is inflated. The laryngeal portion of the back plate on the inner surface may also be known as the laryngeal facing surface. The pharyngeal portion of the back plate on the outer surface may also be known as the laryngeal facing surface. The proximal opening of the back plate is connected to a laryngeal tube (also known herein as the airway tube or the breathing tube).

There is a hole (or opening or aperture) in the roof of the back plate. The hole in the back plate is connected to the laryngeal tube at the proximal end of the laryngeal cuff. The laryngeal tube extends into the tube connector for attachment with the anesthesia bag connector to provide positive pressure ventilation with the bag. The hole in the back plate can be used to advance a catheter through the laryngeal tube and into the larynx and trachea. The laryngeal tube connector will provide communication between the laryngeal tube through laryngeal mask to the larynx and trachea of the infant.

These and further aspects of the neonatal laryngeal airway mask will become apparent in the following discussion and through review of the accompanying figures.

The NLMA is artificial airway device that can be used to facilitate lung ventilation in premature infants smaller than an infant with a gestational age of 30 week or birth weight of 1500 g. The NLMA is an artificial airway device that can be used to facilitate lung ventilation in premature infants with gestational age of 30 weeks to 35 weeks or birth weight of 1500 g to 2500 g. The NLMA is an artificial airway device that can be used to facilitate lung ventilation in infants from gestational age of 35 weeks to 3 months of life or birth weight of 2500 g to 5000 g. This invention is unique in a way that it can be used in term to pre-term infants from greater than 750 gram infants to about 4000 gram infants.

The NLMA can be positioned for sealing an airway tube to the laryngeal inlet of the neonate. This sealing the airway tube to the laryngeal inlet can be used to establish a reliable airway in an emergent situation without the need of endotracheal intubation, as well as to establish an airway for anesthesia administration.

Further, the NLMA can be used to administer surfactant to the lungs of a premature infant suffering from respiratory distress syndrome without into tracheal intubation. The NLMA can be used to introduce a tracheal suction catheter into the trachea of the neonate without endotracheal intubation.

Figure 1:
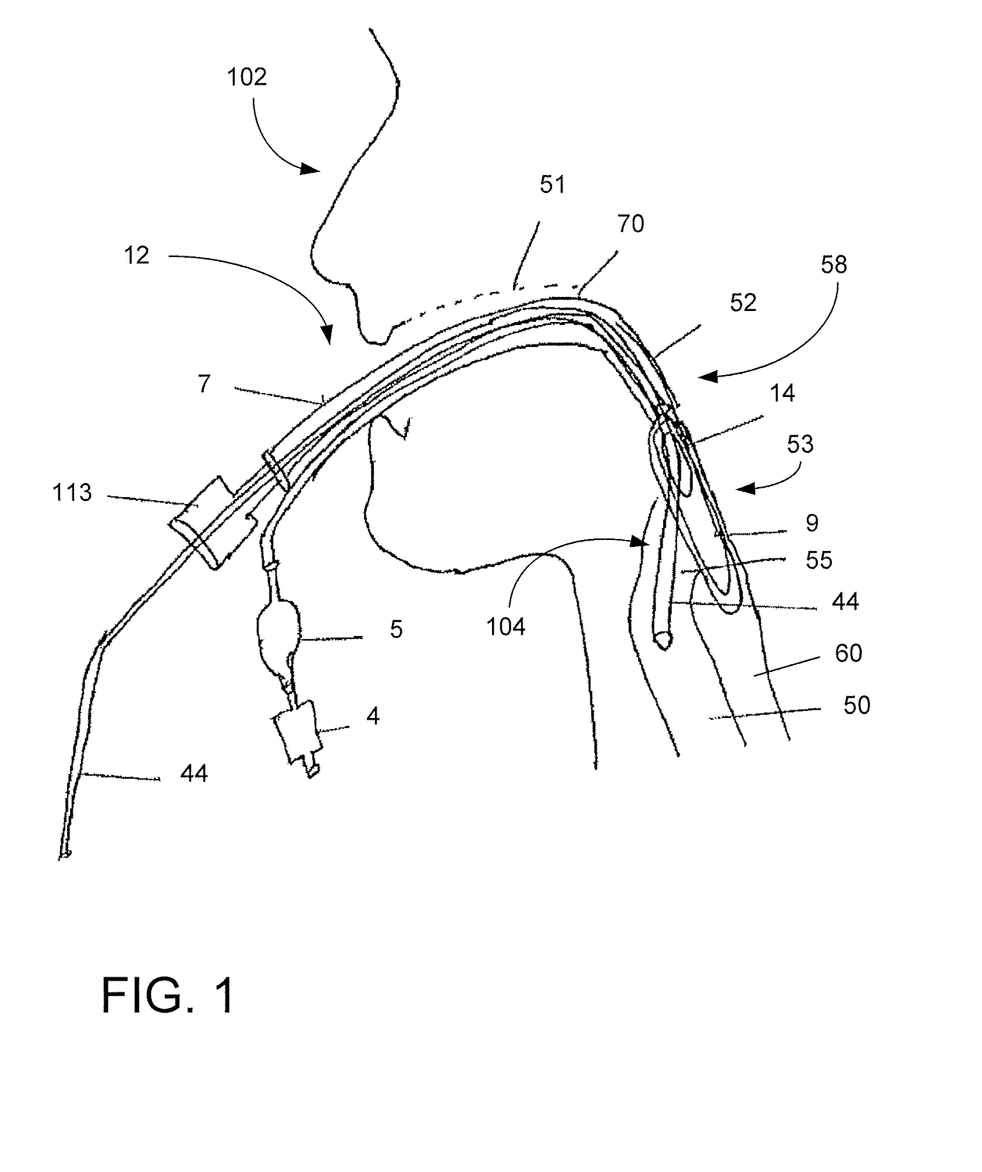
FIG. 1 is a lateral cutaway view of the NLMA in-situ in a patient showing a tracheal catheter is transversely going into the trachea through the glottis opening and an internal-drain tube along the back plate.
Figure 2:
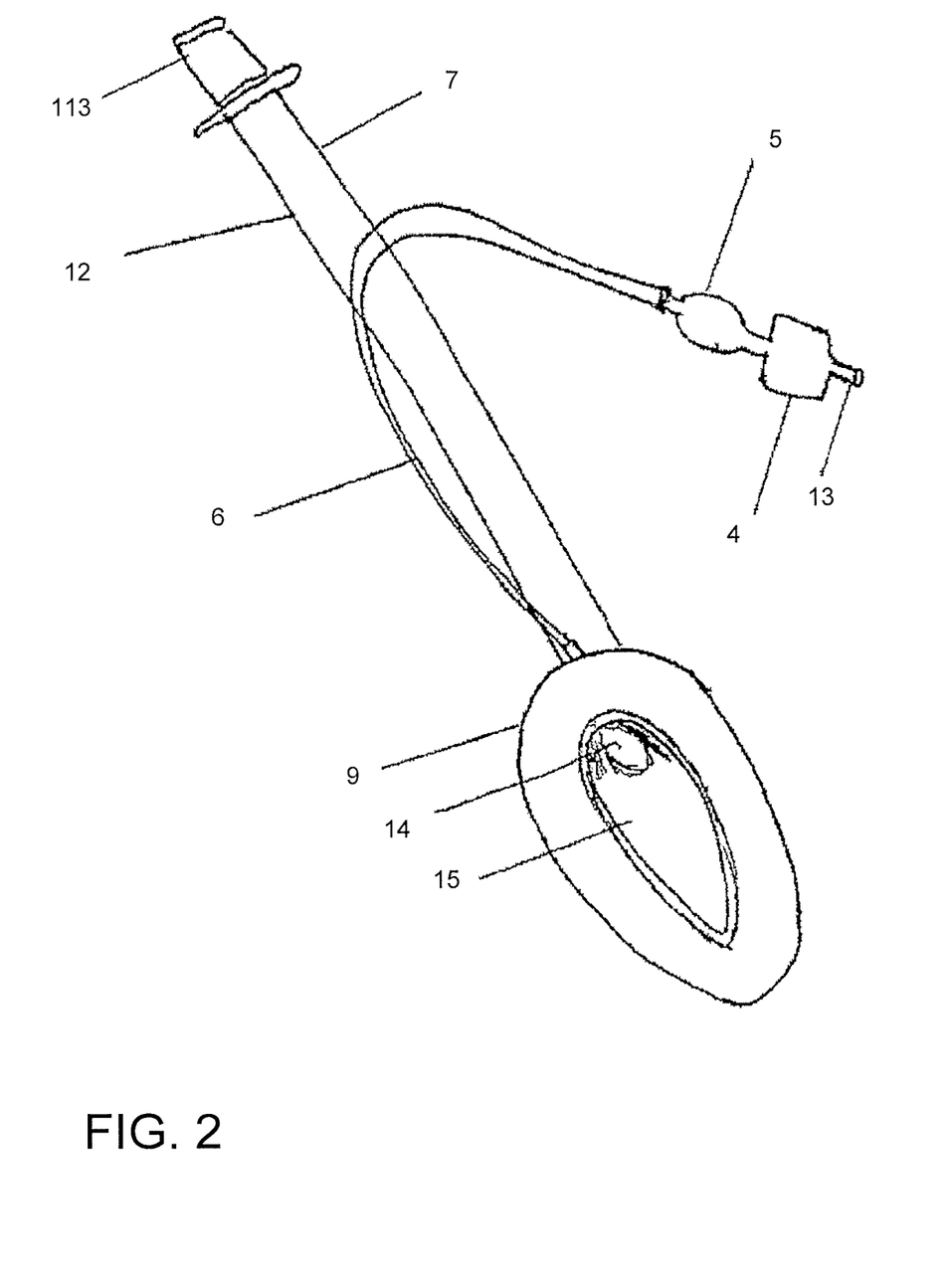
FIG. 2 is a simplified overall view to show the NLMA.

A neonatal laryngeal-mask airway (NLMA) is designated generally by the reference numeral 12 in FIGS. 1 and 2. FIG. 1 shows the NLMA 12 inserted in a patient 102, while FIG. 2 shows the NLMA 12 not in the patient.

The NLMA 12, in a deflated condition, is inserted into the throat 58 the upper surface of which is bounded by hard palate 51 and soft palate 52. In FIG. 1, a tracheal catheter 44 is shown passed through a connector 13, an airway tube (also known herein as the tracheal tube) 7, a laryngeal cuff 9, and a glottis opening 104 into a trachea 50. The tracheal catheter 44 can be used to administer surfactant or can be a tracheal suction catheter. The NLMA 12 is lodged in a pharynx 53 of a throat 58 at the base of a hypo-pharynx 55 where a throat 58 divides into the trachea 50 and an esophagus 60. A lower portion of the NLMA 12 reaches to the base of the hypo-pharynx 55. After the NLMA 12 is lodged in the pharynx 55, the NLMA 12 is inflated to seal the airway tube 7 to an laryngeal inlet 104.

Referring to FIGS. 1 and 2, the NLMA 12 is shown to include the airway tube 7, a back plate 15 having an airway port 14 through which the airway tube 7 can establish a ventilation passageway in the patient 102. The NLMA 12 can pass the tracheal catheter 44 into the trachea 50. The NLMA 12 includes a connector 113 for connection with ventilation equipment, etc.

Figure 3:
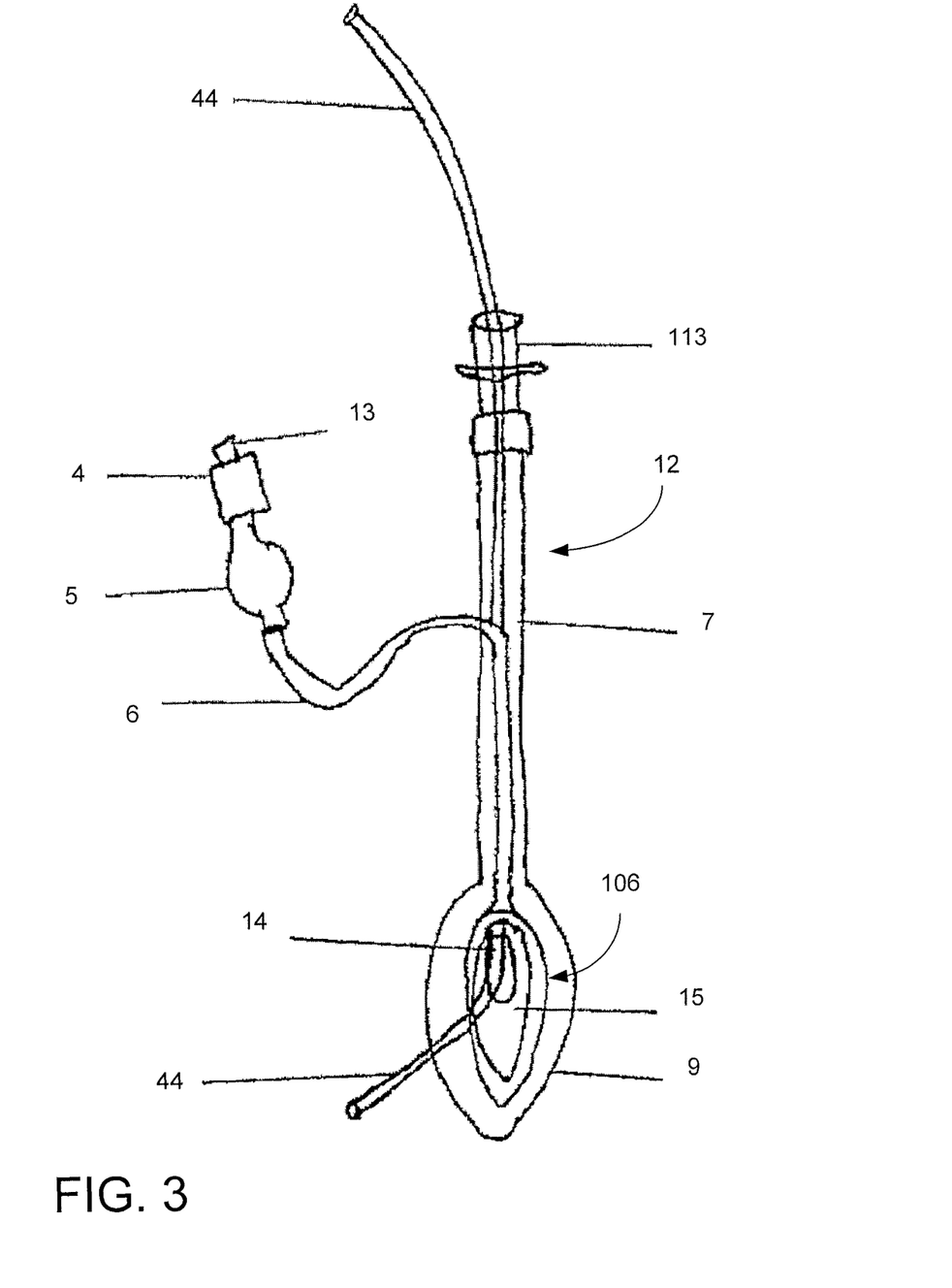
FIG. 3 is a frontal view showing the NLMA of FIG. 1 along with the tracheal catheter in place.

FIG. 3 is a frontal view of the NLMA 12. A perimeter 106 of the back plate 15 is surrounded completely surrounded by a cuff 9. The cuff 9 has an inflatable ring shape that when inflated has an asymmetrical oval shape along the long axis with a narrower portion at the caudal end when the NLMA 12 is positioned in the patient 102 and a wider portion at the rostral end when the NLMA 12 is positioned in the patient 102. The cuff 9 is circumferentially united to the back plate 15 in essentially a single plane, meaning a flat two dimensional plane. There is a communicating hole (also known herein as airway port, back plate opening, or aperture) 14 on a posterior surface of the back plate 15. The posterior surface is behind the plane of the back plate 15 in FIG. 3. The back plate opening is in fluidic communication with the trachea 50 distally and the tracheal tube 7 proximally. The back plate opening 15 facilitates passage of the tracheal catheter 44 into the trachea 50 for the administration of surfactant. There is no ribbing or support structures shown to impair entry of the tracheal catheter 44 into the trachea 50.

An inflation tube 6 and an inflation port 13 are externally accessible on the cuff 9. The inflation tube 6 and the inflation port 13 are the means of supplying air to the cuff 9 to inflate the cuff 9 and of extracting air from (and therefore collapsing) the cuff 9 for purposes of insertion in or removal from the patient 102 of the NLMA 12, respectively. A check-valve 4 is disposed with the inflation tube 7 for holding a given inflation or holding a given deflation of the cuff 9. A balloon 5 is disposed with the inflation tube 7 so that the clinician has an indication whether the cuff 9 is inflated or deflated.

Figures 4A, 4B:
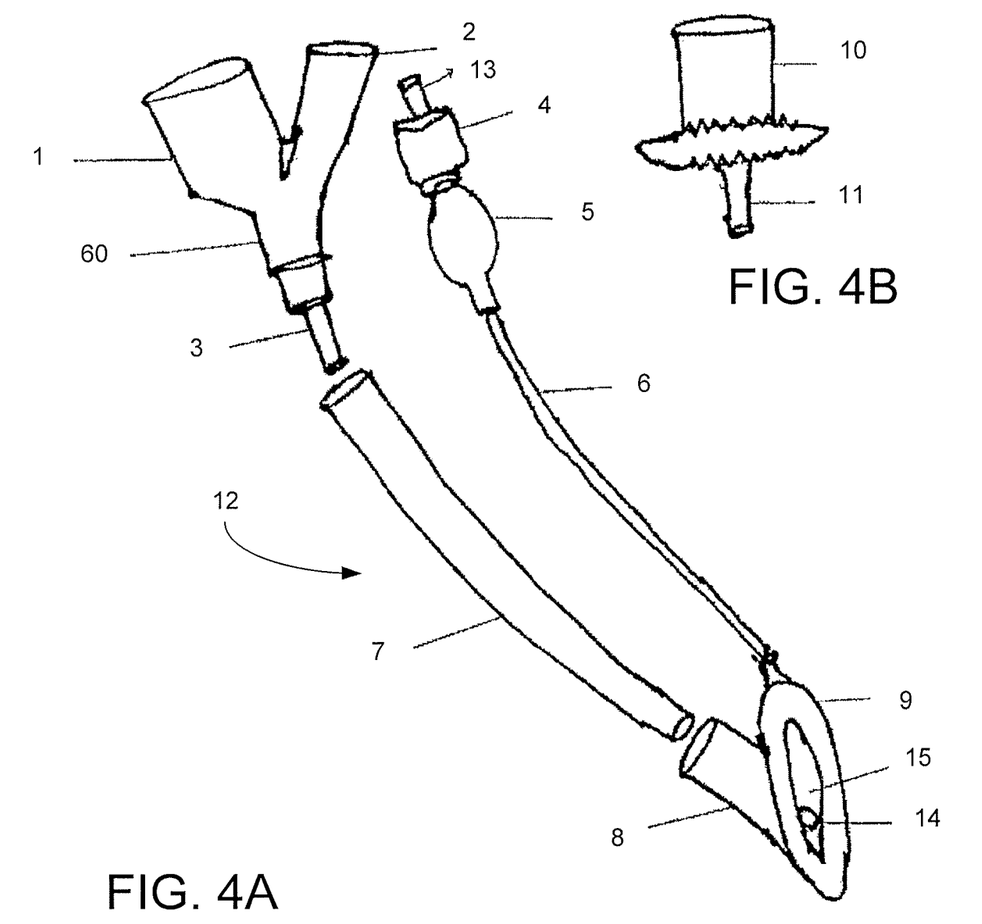
FIGS. 4A-B is a plan view of the anterior side of the NLMA of FIG. 1 showing different parts used with the NLMA.

FIGS. 4A-B shows a double lumen connector 60 that connect to the tracheal tube 7 at the distal end 3 and connects to an anesthesia ventilating bag (not shown) at a proximal end 1. By using the double lumen catheter 60, the tracheal catheter 44 can be introduced into the trachea 50 at a proximal end 2 without disconnecting the ventilation equipment. The tracheal tube 7 can be connected to single lumen connector 10, shown in FIG. 10, with an connection end 11 for connection with the tracheal tube 7 if only airway patency is required.

Figure 5A:
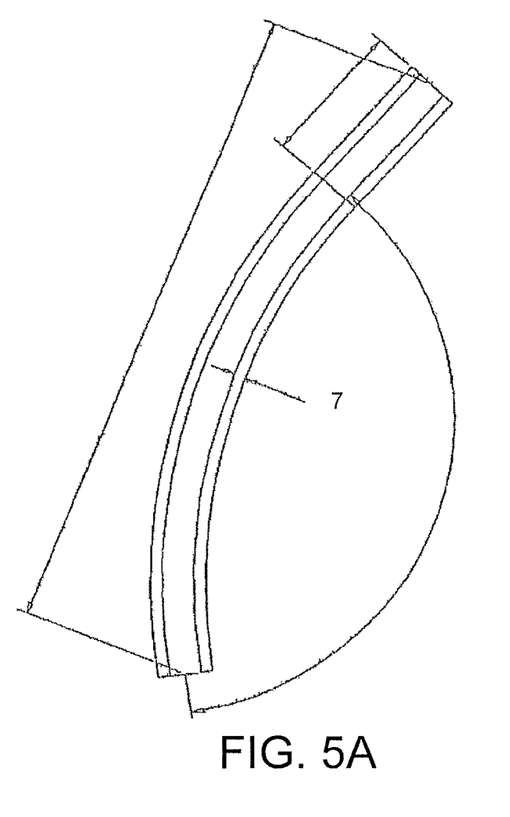
FIGS. 5A-C is an exploded view to show the anterior-posterior dimension of the internal-drain tube relative to a plane containing the anterior surface of the back plate.
Figure 5B:
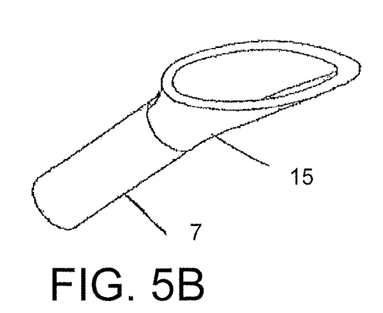
Figure 5C:
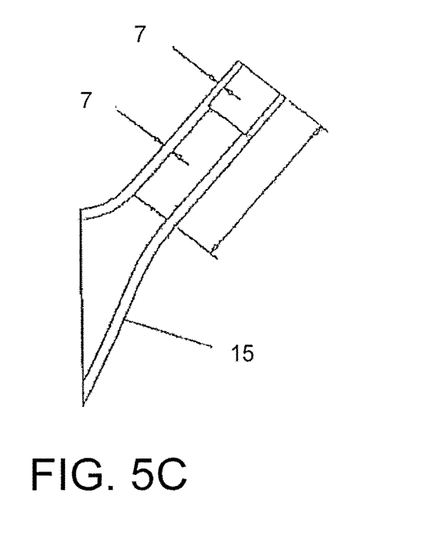

FIGS. 5A-C shows the back plate 15 has a one-piece, integral spoon-shape with an oval shape distally, and the back plate 15 is connected to the tracheal tube 7 at proximal end.

Figure 6A:
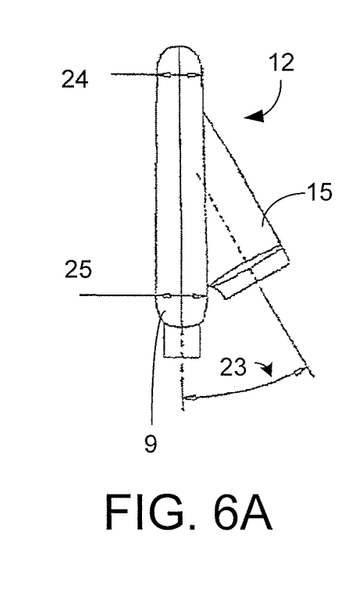
FIGS. 6A-D is a sectional plan view in the plane indicated showing the dimensions of the cuff in anterior-posterior dimension of the NLMA.
Figure 6B:
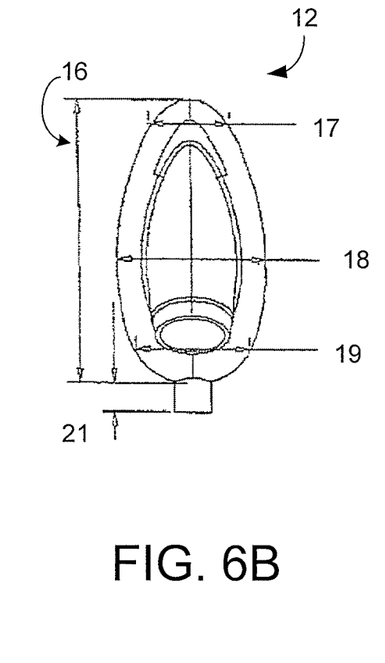
Figure 6C:
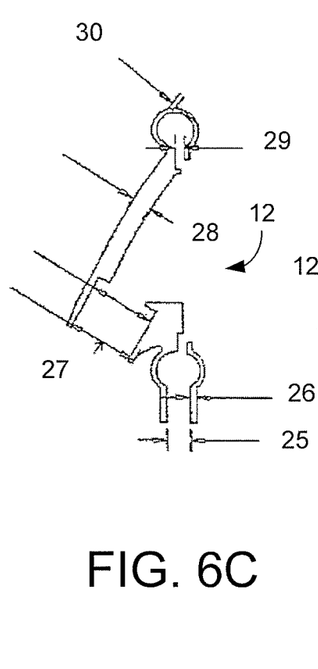
Figure 6D:
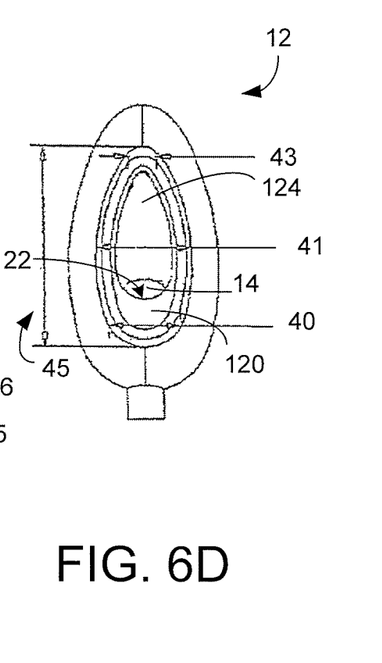
Figure 7A:
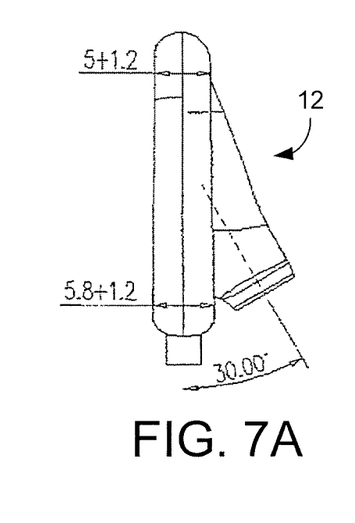
FIGS. 7A-F is a sectional plan view in the plane indicated showing the dimensions of the cuff in anterior-posterior dimension of the NLMA-0.
Figure 7B:
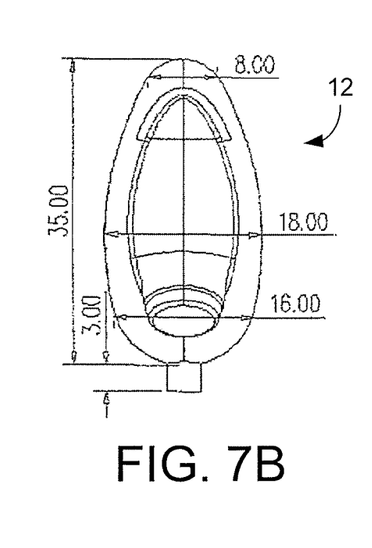
Figure 7C:
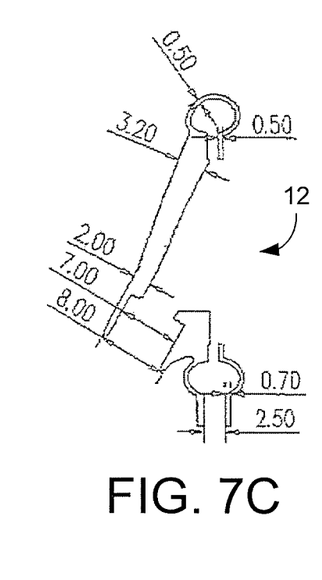
Figure 7D:
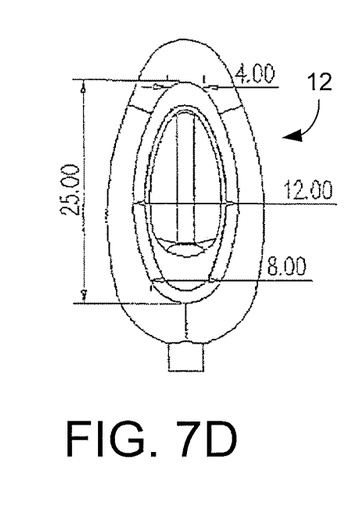
Figure 7E:
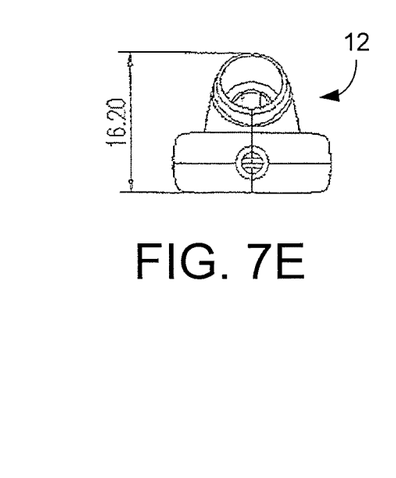
Figure 7F:
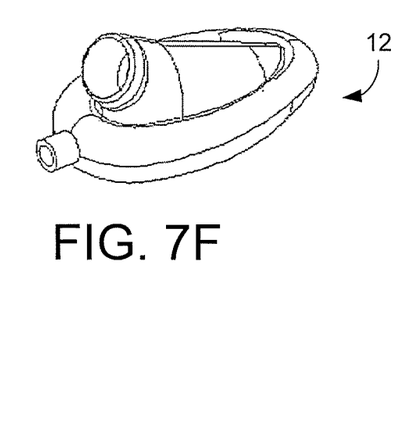
Figure 8A:
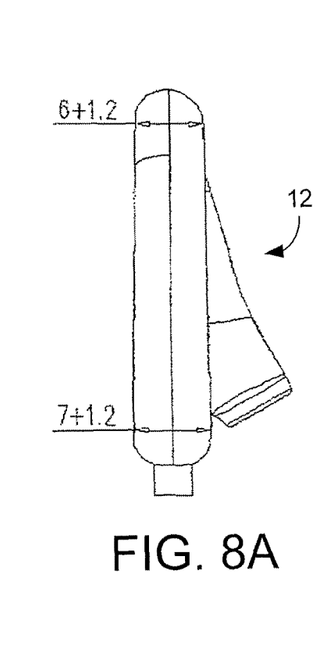
FIGS. 8A-F is a sectional plan view in the plane indicated showing the dimensions of the cuff in anterior-posterior dimension of the NLMA-1.
Figure 8B:
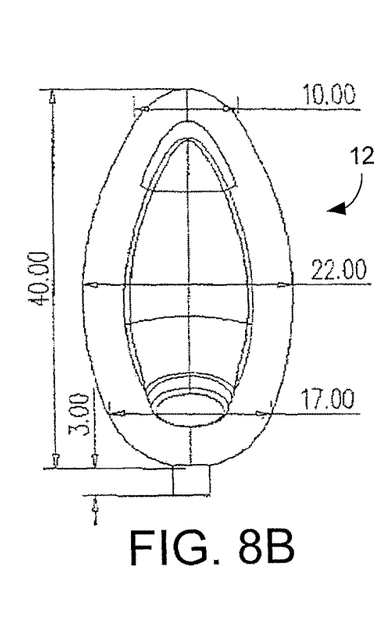
Figure 8C:
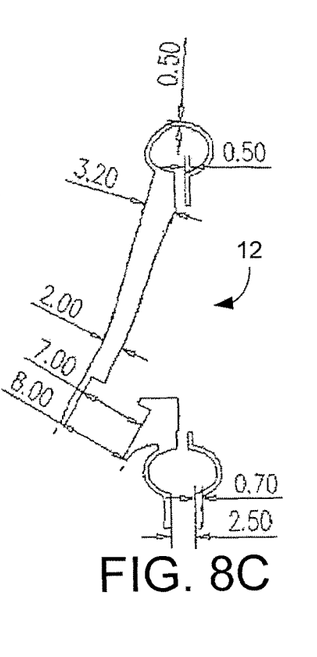
Figure 8D:
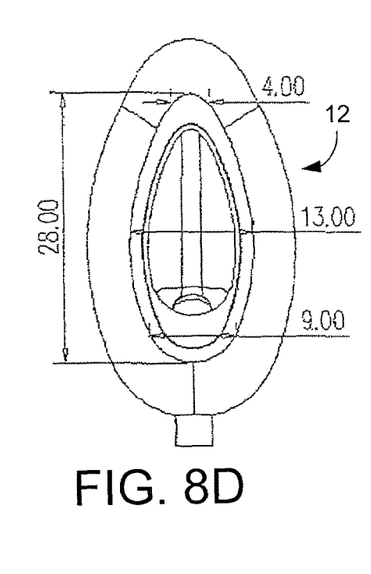
Figure 8E:
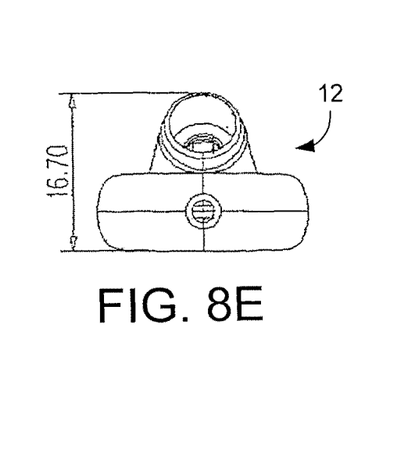
Figure 8F:
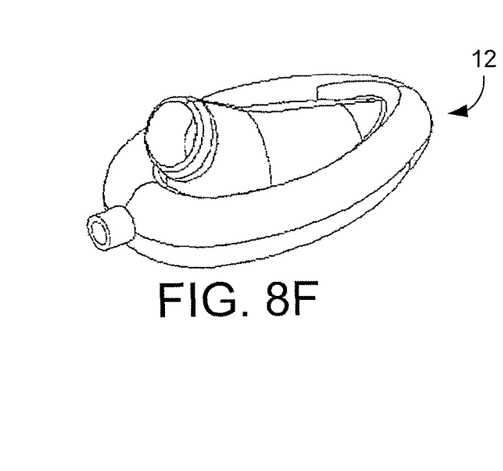

FIGS. 6A-D shows the diagonal dimension of the laryngeal cuff 9 for NLMA. FIG. 6A is a side view of the NLMA 12 showing the back plate and the cuff. FIG. 6B is a top view showing the posterior surface (also known herein as the pharyngeal facing surface to account for this surface primarily facing the pharynx when the NLMA is in the patient) of the back plate 15 and the surrounding cuff 9. FIG. 6C is a cross-section of the NLMA. FIG. 6D is a bottom view showing the anterior (also known herein as the laryngeal facing surface to account for this surface primarily facing the larynx when the NLMA is in the patient or alternatively the surface can be known as the glottis facing surface to account for this surface primarily facing the glottis when the NLMA is in the patient). The NLMA 12 has dimensions that include: vertical external length 16, anterior external diameter in horizontal plane 17, middle external diameter in horizontal plane 18, posterior external diameter in horizontal plane 19, distal cuff diameter 24, proximal cuff diameter 25 posterior end of the cuff internal diameter in horizontal plane 40, wall thickness 26 for entry port into the cuff, exterior diameter 27 of the entry port for the tracheal tube into the back plate 15, wall thickness 28 of the back plate 15, distal cuff diameter 29 distal end of the cuff, cuff wall thickness 30, middle internal diameter in horizontal plane 41, anterior internal diameter in horizontal plane 43, and internal cuff length 45.

FIG. 6D perhaps provides the best view of a shelf 120 and going into the plane of the figure a wall 122. The shelf 120 is parallel to the horizontal plane of the back plate 15. The back plate 15 provides a perimeter in a first flat two dimensional plane. The shelf 120 is in a second flat two dimensional plane that is parallel to and different from the first flat two plane. The wall 122 is perpendicular to the shelf 120. The wall 122 partially surrounds the back plate opening 14. The wall 122 extends from the back plate 15 to the shelf 120 an entire or complete distance between the back plate opening 14 and the shelf 120. Further, a channel 124 can be seen in this view. The channel 124 is a concave surface that can help guide the catheter being passed through the NLMA. The guidance can help direct the catheter into the trachea, as previously discussed. The cooperation between the wall 122 and the shelf 120 allows a depth to the channel 124 that helps guide the catheter into position, for example.

FIGS. 7A-F shows the dimensions of NLMA-0. The cuff 9 has the following external dimensions: the anterior external dimension in horizontal plane 17 is 8 millimeter (mm), the posterior external dimension in horizontal plane 19 is 16 mm, the middle external dimension in horizontal plane 18 is 16 mm, and the vertical external length 16 is 35 m. The cuff 9 has the following internal dimensions: the anterior internal horizontal diameter 43 is 4 mm, the posterior end of the cuff internal horizontal dimension 40 is 8 mm, the internal cuff length 45 is 25 mm. An angle 23 between the cuff 9 and the back plate 15 is 30 degree angle. The cuff is fused at acute angle of 30 degree at the back plate in a way so it can be in close proximity to laryngeal opening. The tracheal tube tube 7 is 7 mm in external diameter and 0.5 mm in internal diameter. When inflated, the laryngeal cuff 9 has a thickness of 5+1.2 mm at the distal end 24 and 5.8+1.2 mm at the proximal end 25 of the cuff 9 where it is connected to the breathing tube. When not inflated, the laryngeal cuff 9 has thickness of 5 mm at the distal end 24 and 5.8 mm at the proximal end 25.

FIGS. 8A-F shows the diagonal dimension of NLMA-1. The cuff 9 has the following external dimensions: the anterior external diameter in horizontal plane 17 is 10 millimeter, the posterior external diameter in horizontal plane 19 is 17 millimeter, the middle external diameter in horizontal plane 18 is 22 millimeter, and the vertical external length 16 is 40 millimeter. The cuff 9 has the following internal dimensions: the anterior internal diameter in horizontal plane 43 is 4 millimeter, the posterior end of the cuff internal diameter in horizontal plane 40 is 9 millimeter, and the internal cuff length 45 is 28 millimeter. The angle 23 between the cuff 9 and the back plate 15 is 30°. The cuff is fused at acute angle of 30 degree at the back plate in a way so it can be in close proximity to laryngeal opening. The tracheal tube 7 is 7 mm in external diameter and 0.5 millimeter in internal diameter. When inflated, the laryngeal cuff 9 has a thickness is 6+1.2 millimeter at the distal end 24 and 7+1.2 millimeter at the proximal end 25 where it is connected to the breathing tube. When not inflated, the laryngeal cuff 9 has a thickness of 6 mm at the distal end 24 and 7 mm at the proximal end 25.

What is claimed is:

1. An apparatus comprising:
   a back plate that provides
      a perimeter in a first flat two dimensional plane,
      a shelf in a second flat two dimensional plane that is parallel to and different from the first flat two dimensional plane, wherein a diameter of the perimeter in the first flat two dimensional plane is greater than a diameter of the shelf in the second flat two dimensional plane,
      a back plate opening,
      a wall that extends perpendicularly to the shelf and surrounds less than all of the back plate opening, wherein the wall perpendicularly extends completely from the back plate opening to the shelf; and
   a cuff extended completely around the perimeter, the cuff configured for inflation from an uninflated state to an inflated state in a patient with a pharynx, a larynx with a laryngeal inlet, and a trachea to form a seal around the laryngeal inlet to isolate the larynx from the pharynx, and the back plate is configured to guide a catheter inserted through the back plate opening into the trachea, wherein cooperation between the shelf and the wall, which remain perpendicular to each other during use in the patient, forms a channel that is configured to guide the catheter into engagement with a concave surface of the back plate to guide the catheter into the trachea, and the shelf is configured to be in fluid communication with the trachea.

2. The apparatus of claim 1, wherein the patient has lungs, and the back plate is configured to guide the catheter upon insertion through the back plate opening into the lungs for administration of surfactant into the lungs.

3. The apparatus of claim 1, wherein further comprising:
   an entry port coupled to the back plate opening, the entry port has central long axis that is oriented at a 30° angle from the perimeter of the back plate.

4. The apparatus of claim 1, wherein the patient is a neonate smaller than an infant with a gestational age of 30 weeks.

5. The apparatus of claim 1, wherein the patient is a neonate with a gestational age of 30 weeks to 35 weeks.

6. The apparatus of claim 1, the back plate has a length axis longer than a width axis that is perpendicular to the length axis, and a first end narrower than a second end along the length axis, wherein when the back plate is inserted into the neonate, the second end of closer than the first end to a head of the neonate.

7. The apparatus of claim 1, the back plate has a length axis longer than a width axis that is perpendicular to the length axis, and a first end narrower than a second end along the length axis, wherein the shelf is positioned closer to the second end than the first end.

8. A neonatal laryngeal mask airway comprising:
   a back plate with a perimeter that lies in a first flat two dimensional plane;
   an opening in the back plate configured for passage of a catheter;
   a shelf that lies in a second flat two dimensional plane parallel to and different from the first flat two dimensional plane, the shelf is inside the perimeter and the second flat two dimensional plane is closer to the opening than the first flat two dimensional plane is to the opening;
   a wall extends perpendicularly from the shelf all the way to the opening, wherein the wall incompletely surrounds the opening;
   a channel in the back plate formed by cooperation of the shelf and the wall; and
   an inflatable cuff coupled to the back plate, the inflatable cuff is configured for insertion in an uninflated state into a neonate with a pharynx, a larynx with a laryngeal inlet, a trachea, and lungs, and for formation of a seal in an inflated state around the laryngeal inlet to isolate the larynx from the pharynx except for fluid communication through the opening in the back plate, and the back plate in cooperation with the channel is configured to guide the catheter through the opening upon insertion into the trachea for administration of surfactant into the lungs, and the neonatal laryngeal mask airway is dimensioned to fit the neonate so that the shelf and the wall remain perpendicular during use in the neonate, wherein the shelf is configured to be in fluid communication with the trachea.

9. The neonatal laryngeal mask airway of claim 8, the back plate has a length axis longer than a width axis that is perpendicular to the length axis, and a first end narrower than a second end along the length axis, wherein when the back plate is inserted into the neonate, the second end of closer than the first end to a head of the neonate.

10. The neonatal laryngeal mask airway of claim 8, the back plate has a length axis longer than a width axis that is perpendicular to the length axis, and a first end narrower than a second end along the length axis, wherein the shelf is positioned closer to the second end than the first end.

11. The neonatal laryngeal mask airway of claim 8, wherein the opening is configured for passage of the catheter at an angle of 30° from the first flat two dimensional plane.

12. The neonatal laryngeal mask airway of claim 8, wherein the channel is configured to guide the catheter inserted through the opening into engagement with a concave surface of the back plate to guide the catheter past the inflatable cuff in the inflated state into the trachea.

13. The neonatal laryngeal mask airway of claim 8, wherein the neonate is greater than 750 g to about 4000 g.

14. A neonatal laryngeal mask airway comprising:
   a back plate with a perimeter lies in a first flat two dimensional plane;
   an entry port in the back plate is configured for entry of a catheter;
   a shelf lies in a second flat two dimensional plane that is parallel to and different from the first flat two dimensional plane, wherein the first flat two dimensional plane is located towards the entry port in relation to the perimeter;
   a wall extends perpendicularly from the entry port to the shelf; and
   an inflatable cuff coupled to the back plate, and wherein the shelf and the wall remain perpendicular during use in a neonate, and the shelf is configured to be in fluid communication with a trachea of the neonate.

15. The neonatal laryngeal mask airway of claim 14, wherein the shelf is inside the perimeter.

16. The neonatal laryngeal mask airway of claim 14, wherein the back plate is configured to guide the catheter through the entry port the inflatable cuff is configured for insertion in an uninflated state into a neonate with a pharynx, a larynx with a laryngeal inlet, a trachea, and lungs, and for formation of a seal in an inflated state around the laryngeal inlet to isolate the larynx from the pharynx except for fluid communication through the entry port in the back plate.

17. The neonatal laryngeal mask airway of claim 14, further comprising:
   a channel in the back plate formed by cooperation of the shelf and the wall is configured to guide the catheter through the entry port for insertion into the trachea for administration of surfactant into lungs of the neonate.

18. The neonatal laryngeal mask airway of claim 14, wherein the neonate is greater than 750 g to about 4000 g with lungs, and cooperation between the shelf and the wall forms a channel that is configured to guide the catheter inserted through the back plate opening into engagement with a concave surface of the back plate to guide the catheter into the trachea.

19. The neonatal laryngeal mask airway of claim 14, the back plate has a length axis longer than a width axis that is perpendicular to the length axis, and a first end narrower than a second end along the length axis, wherein when the back plate is inserted into the neonate, the second end of closer than the first end to a head of the neonate.

20. The neonatal laryngeal mask airway of claim 14, the back plate has a length axis longer than a width axis that is perpendicular to the length axis, and a first end narrower than a second end along the length axis, wherein the shelf is positioned closer to the second end than the first end.

* * * * *